United States Patent
Poole et al.

(10) Patent No.: US 7,140,365 B2
(45) Date of Patent: *Nov. 28, 2006

(54) INHALATION APPARATUS

(75) Inventors: Trent Poole, South Amherst, MA (US); Solomon S. Steiner, Mount Kisco, NY (US)

(73) Assignee: MannKind Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/118,853

(22) Filed: Apr. 29, 2005

(65) Prior Publication Data

US 2005/0188988 A1    Sep. 1, 2005

Related U.S. Application Data

(63) Continuation of application No. 10/384,909, filed on Mar. 7, 2003, now Pat. No. 6,923,175.

(60) Provisional application No. 60/366,302, filed on Mar. 20, 2002.

(51) Int. Cl.
*A61M 11/00* (2006.01)
*B67D 5/60* (2006.01)

(52) U.S. Cl. ............... 128/200.14; 128/200.17; 222/144

(58) Field of Classification Search ........... 128/200.24, 128/200.11, 200.12, 200.14, 200.17, 200.21, 128/200.23, 203.12, 203.14, 203.15, 203.18, 128/203.19, 203.21, 204.12, 206.11, 200.22, 128/144; 222/153.01, 519, 160, 165, 635

See application file for complete search history.

(56) References Cited

U.S. PATENT DOCUMENTS

| | | |
|---|---|---|
| 4,175,556 A | 11/1979 | Freezer |
| 5,250,287 A | 10/1993 | Cocozza |
| 5,287,850 A | 2/1994 | Haber et al. |
| 5,351,683 A | 10/1994 | Chiesi et al. |
| 5,352,461 A | 10/1994 | Feldstein et al. |
| 5,394,868 A | 3/1995 | Ambrosio et al. |
| 5,503,852 A | 4/1996 | Steiner et al. |
| 5,533,502 A | 7/1996 | Piper |
| 5,584,417 A | 12/1996 | Graf et al. |
| 5,634,900 A | 6/1997 | Makino et al. |
| 5,642,727 A | 7/1997 | Datta et al. |
| 5,699,789 A | 12/1997 | Hendricks |
| 5,746,227 A | 5/1998 | Rose et al. |
| 5,996,577 A | 12/1999 | Ohki et al. |
| 6,071,497 A | 6/2000 | Steiner et al. |
| 6,198,847 B1 | 3/2001 | Washizawa |
| 6,298,847 B1 | 10/2001 | Datta et al. |
| 6,484,715 B1 | 11/2002 | Ritsche et al. |
| 6,722,363 B1 | 4/2004 | Von Schuckmann |
| 6,748,946 B1 | 6/2004 | Rand et al. |
| 6,923,175 B1 * | 8/2005 | Poole et al. ........... 128/200.14 |

FOREIGN PATENT DOCUMENTS

WO    WO 97/30743    8/1997

* cited by examiner

*Primary Examiner*—Teena Mitchell
(74) *Attorney, Agent, or Firm*—Pabst Patent Group LLP

(57) ABSTRACT

An inhaler is instantly activated upon its removal from a cover or cover unit, and by rotating a cartridge component of the inhaler with respect to a mouthpiece portion, so as to create a flow pathway for ambient air and particles. The cartridge component includes a chamber, whose contents typically include dry powders or the like. Upon creation of the flow pathway, the contents of the chamber are instantly accessible for immediate inhalation by a user through the mouthpiece portion.

2 Claims, 8 Drawing Sheets

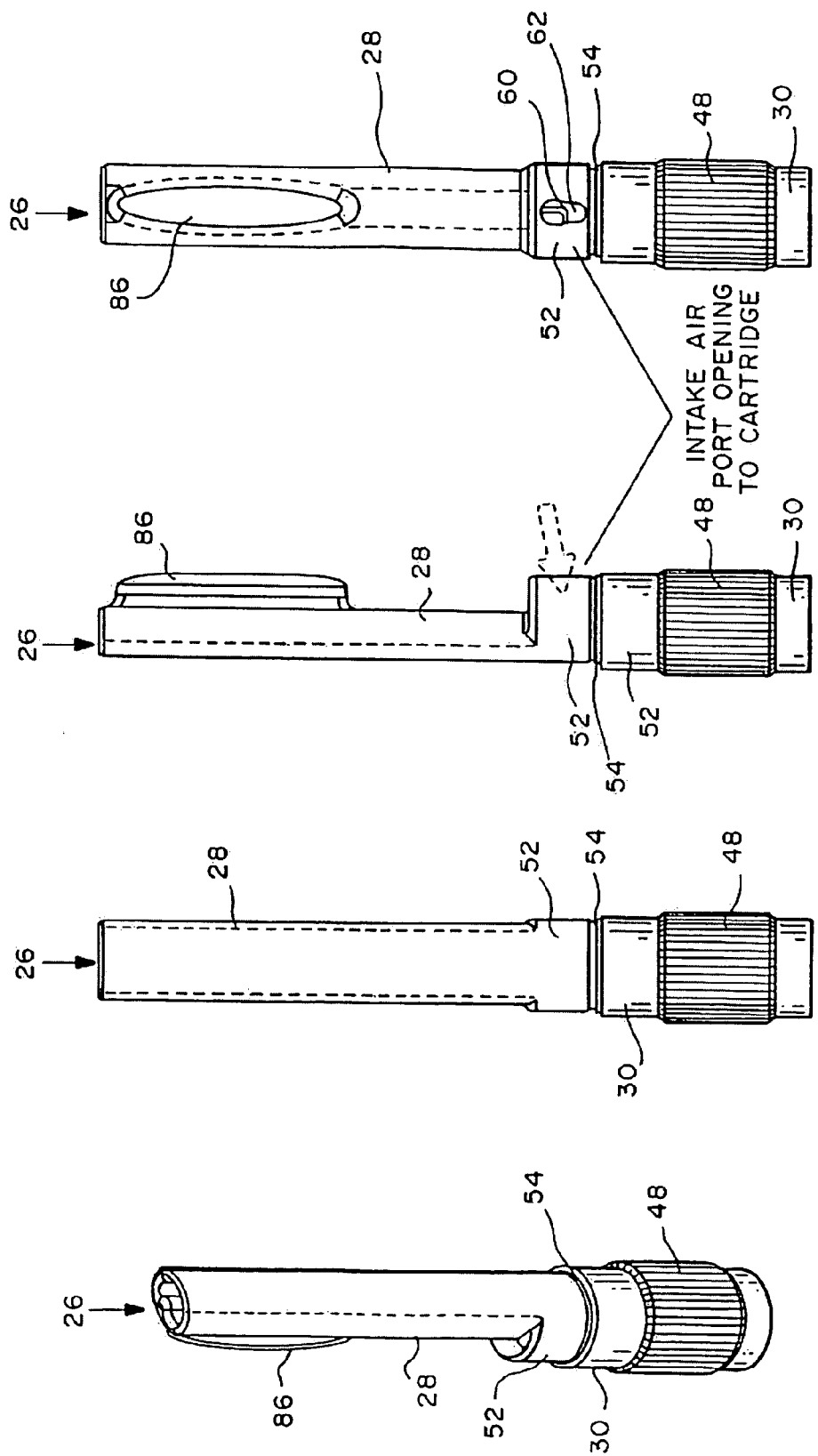

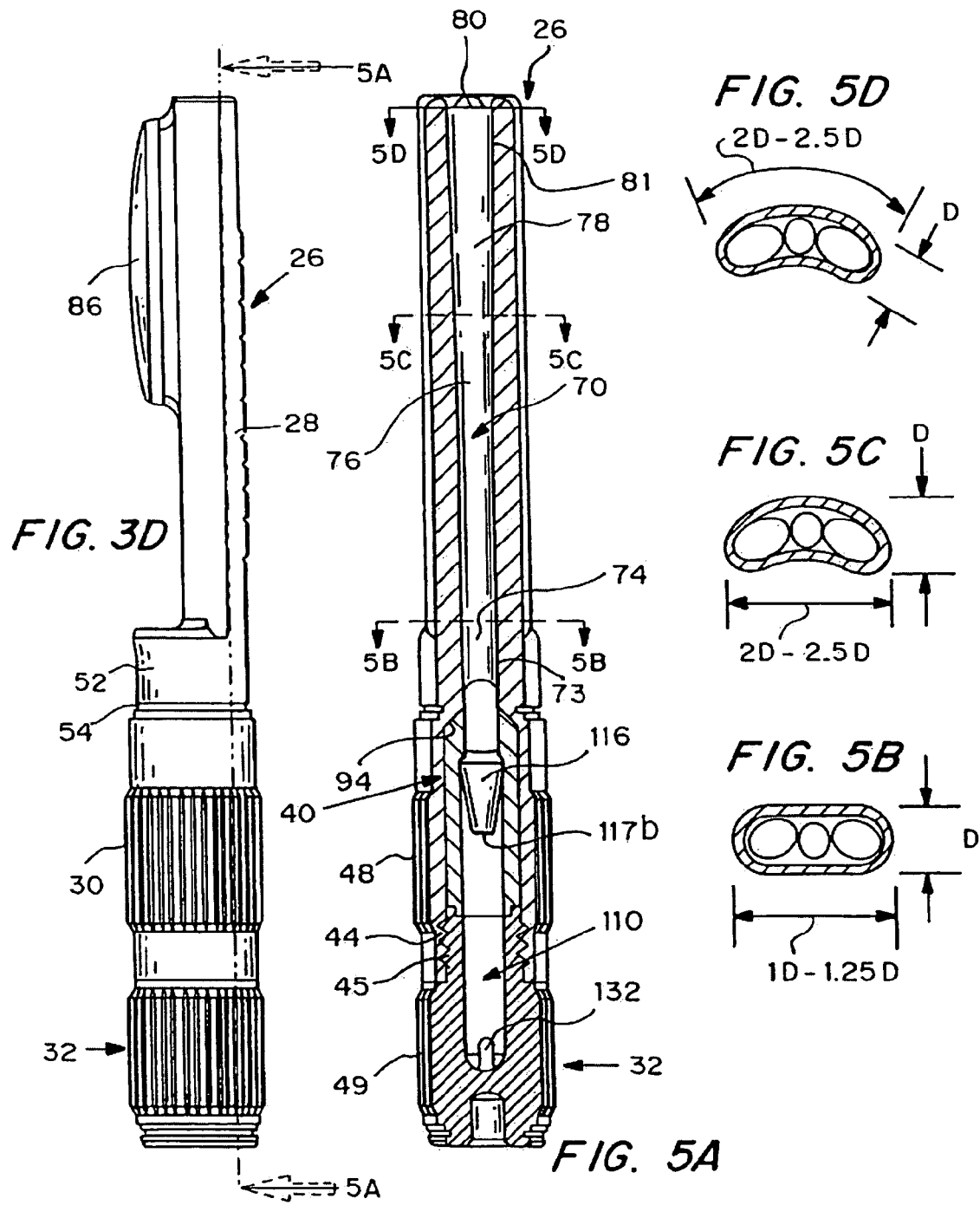

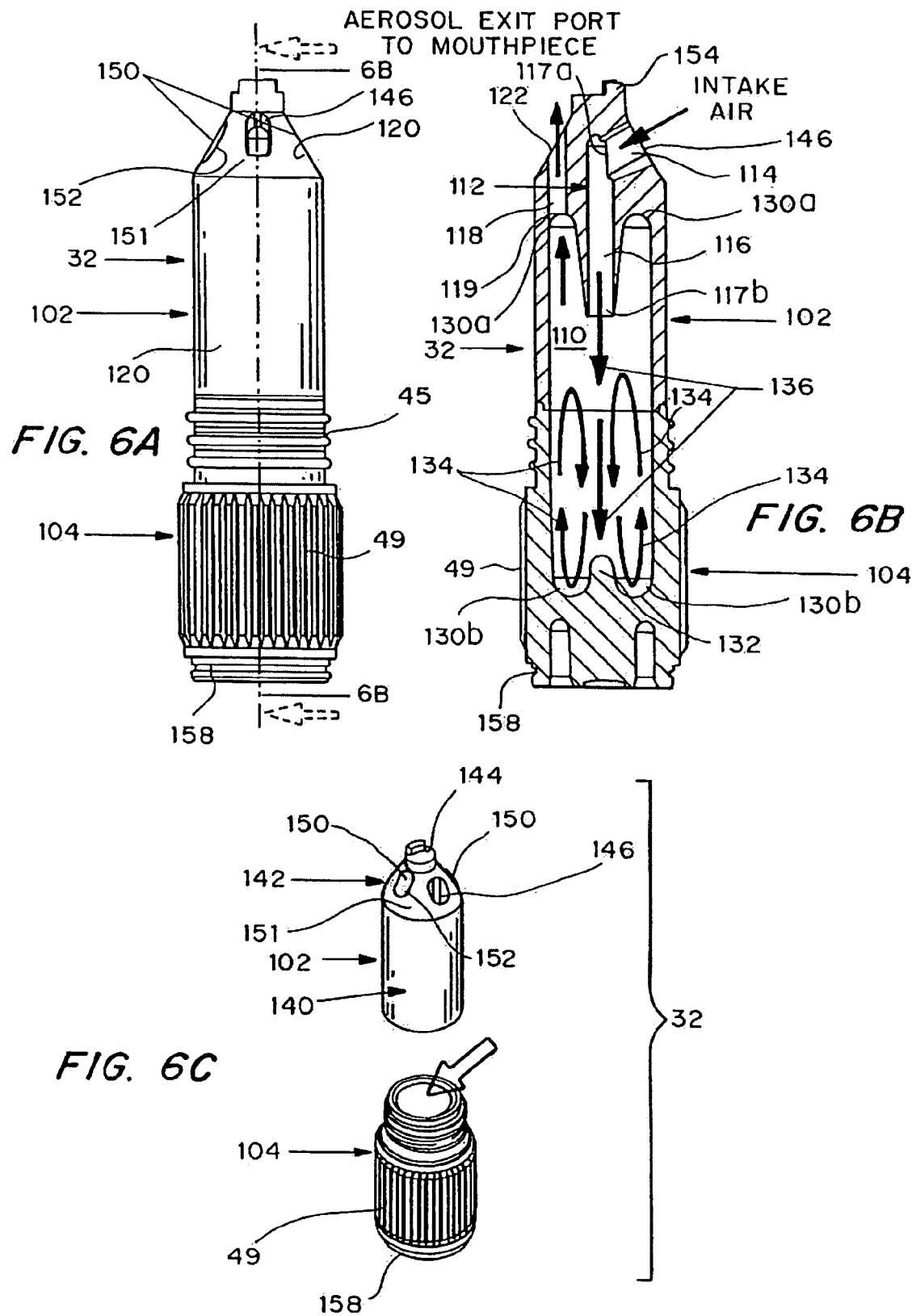

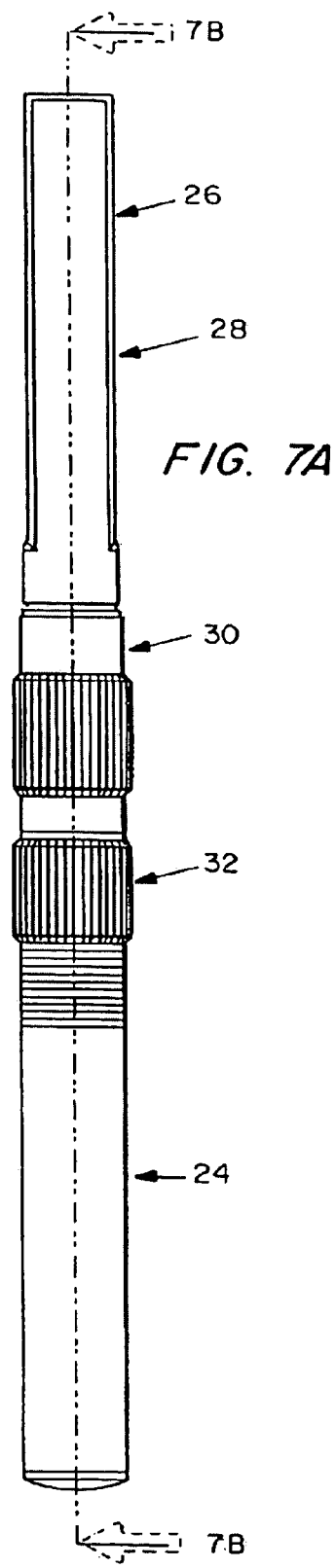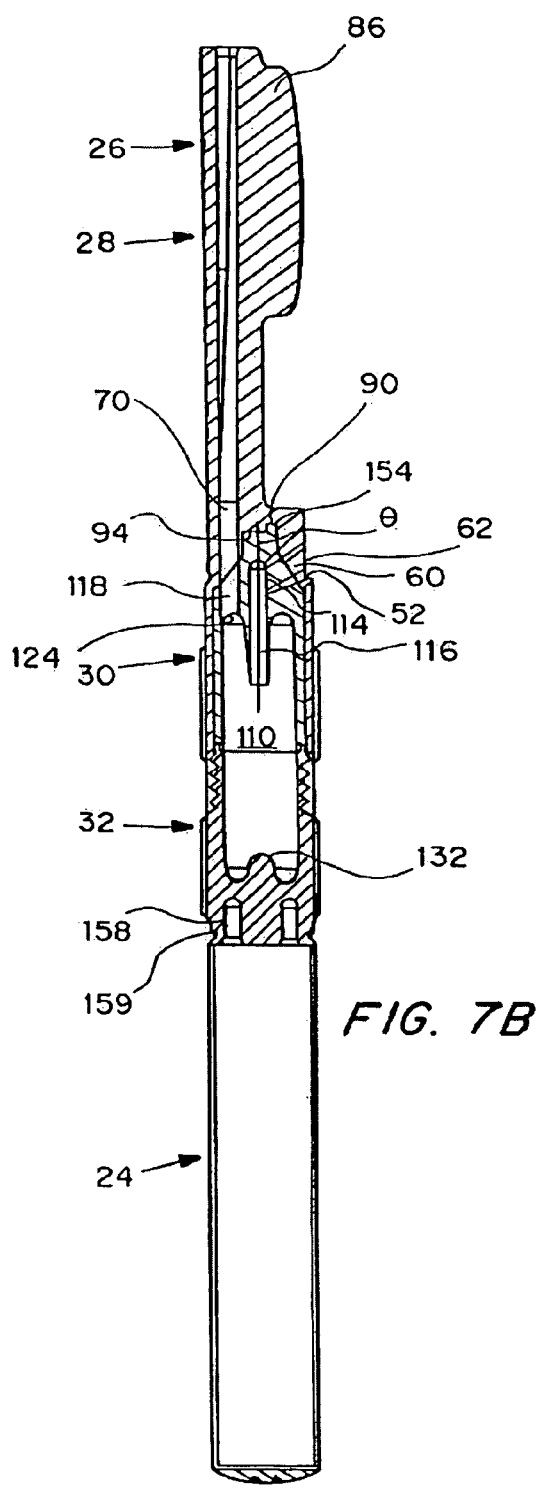

INHALATION APPARATUS

This is a continuation of U.S. Ser. No. 10/384,909 filed Mar. 7, 2003 entitled "Inhalation Apparatus" by Trent Poole and Solomon S. Steiner (now U.S. Pat. No. 6,923,175); which claims priority to U.S. Provisional Application Ser. No. 60/366,302 filed Mar. 20, 2002.

TECHNICAL FIELD

The present invention is directed to inhalers, and in particular to dry powder inhalers.

BACKGROUND

Inhalers or inhalation devices that deliver their content in the forms of liquid mists and powder in aerosol forms, are in common use today. However, these inhalers typically employed propellants, whose effectiveness is pressure, and thus, altitude and atmospherically dependent. Additionally, propellants such as chlorofluorocarbon propellants are banned by treaties, as they are harmful to the environment.

As a result, dry powder inhalers or inhalation devices were developed. However, these dry powder inhalers were of limited use, especially when delivery of medication to the deep lung was desired.

These dry powder inhalers exhibited drawbacks in that their design resulted in particles moving too fast or agglomerating. When particles traveled too fast, they typically struck the back of the throat, where they were swallowed, without ever reaching the lungs. Similarly, particles that agglomerated were too heavy, and typically fell out of the inhaled breath stream in the mouth or oral cavity, where they were swallowed without ever reaching the lungs. Accordingly, the powder, if any, that reached the lungs was typically in amounts ineffective for proper treatment.

Moreover, these conventional inhalers are relatively large. As a result of this large size, their portability, in pockets and other compartments is limited, and to a greater extent, the space required for their use is large. For example, the space required for use of these conventional inhalers would make them difficult, if not impossible to use under a gas mask or the like, as the airspace therein is extremely limited. Coupled with the amount of space taken up in pockets, first aid kits, etc., many of these conventional inhalers are not suited for battlefield and other emergency uses.

SUMMARY

The apparatus, components and methods disclosed herein improve on the contemporary art by providing a dry powder inhaler whose contents can reach the lungs in amounts effective for treatment of various conditions. The apparatus disclosed herein includes an inhaler (inhaler portion) that utilizes the user's breath to pass the dry powder from the body of the device to the lungs of the user, eliminating the need for propellants. Accordingly, the inhaler disclosed herein can be used regardless of altitude and atmospheric conditions.

The inhaler disclosed herein is of a configuration, that when the user's breath reaches a sufficient predetermined flow rate, the dry powder contained therein will deagglomerate. These deagglomerated dry powder particles are then entrained in the inhaled breath stream, allowing for the contents of the inhaler to reach the lungs in effective amounts.

The inhaler is small and compact. This small size enables use in small spaces. For example, the inhaler can be placed under, or inserted into, a gas mask or other protection device, to utilize the closed airspace therein, without disrupting its function. The inhaler can also be for single or one-time uses and can be disposable.

The inhaler is instantly activated, upon its removal from a cover or cover unit. The inhaler detaches from the cover by simply pulling it in a direction away from the cover or by rotation, if a high helix thread engagement is present on the cover and inhaler. By rotating a cartridge component of the inhaler, where inhaler medication is stored in a chamber, a channel is opened from this chamber to the ambient environment. In addition, the storage chamber is opened to the mouthpiece, providing immediate access to the chamber contents for immediate inhalation.

The inhaler is sanitary and its contents are protected until use, as the mouthpiece and opening to the ambient environment are under a cover, that engages the body of the inhaler in a locking arrangement until use is desired. Each inhaler can be individually covered, or the individual covers can be attached so as to be a single unit with formed of multiple covers with corresponding inhalers.

BRIEF DESCRIPTION OF THE DRAWINGS

Attention is now directed to the drawing figures, where like reference numerals or characters indicate corresponding or like components. In the drawings:

FIG. 3A is an isometric view of the mouthpiece of FIG. 2;

FIG. 3B is a front view of the mouthpiece of FIG. 2;

FIGS. 3C and 3D are side views of the mouthpiece of FIG. 2;

FIG. 3E is a rear view of the mouthpiece of FIG. 2;

FIG. 5A is a view of the mouthpiece of FIG. 3D, taken along line 5A—5A;

FIGS. 5B, 5C, 5D are cross sectional views of FIG. 5A, taken along lines 5B—5B, 5C—5C and 5D—5D, respectively;

FIG. 6A is a front view of the cartridge of FIG. 2;

FIG. 6B is a view of the cartridge of FIG. 6A taken along line 6B—6B;

FIG. 6C is an exploded view of the cartridge of FIG. 6A;

FIG. 7A is a front view of the apparatus of FIG. 1 with the cover repositioned on the inhaler portion;

FIG. 7B is a cross-sectional view of the apparatus of FIG. 7A taken along line 7B—7B;

DETAILED DESCRIPTION OF THE DRAWINGS

Figure 1:
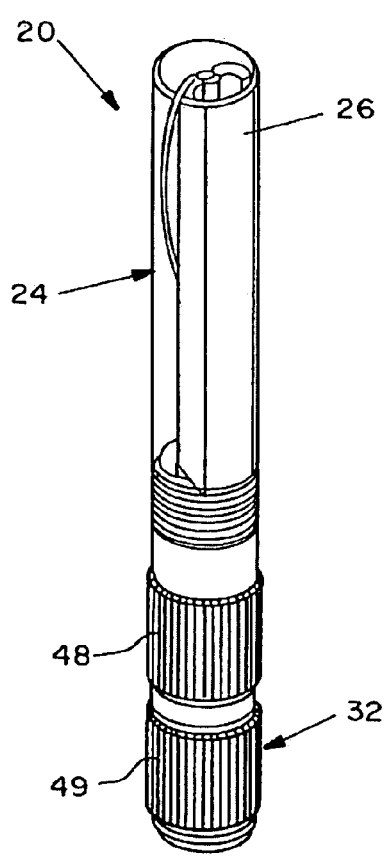
FIG. 1 is an isometric view of an embodiment of the apparatus disclosed herein as a single unit.
Figure 2:
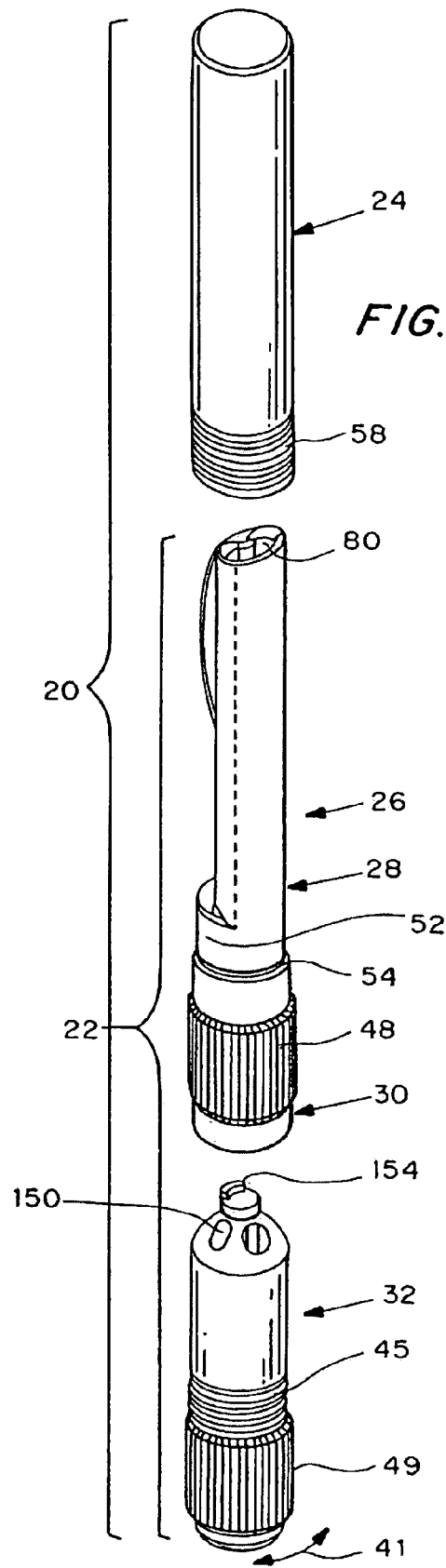
FIG. 2 is an exploded view of the device of FIG. 1.

FIGS. 1 and 2 show an apparatus 20 formed from an inhaler portion (inhaler) 22 and a cover 24. The inhaler portion 22 includes a mouthpiece 26, formed of a tube section 28 and a body section 30, and a cartridge 32. The mouthpiece 26 includes an interior bore 40 (FIGS. 4 and 5A) for receiving the cartridge 32 in a frictional and rotatable engagement, allowing for rotation of the cartridge 32 with respect to the mouthpiece 26, and vice versa (in accordance with double headed arrow 41). This engagement is maintained by correspondingly positioned riblets 44 (FIGS. 4 and 5A), 45 on the mouthpiece 26 and cartridge 32, that engage each other. Both the mouthpiece 26 and cartridge 32 include ridged collar sections 48, 49 to facilitate gripping by the user, in order to rotate the cartridge 32 in the mouthpiece 26.

The cover 24 typically attaches to the inhaler portion 22 at the shank 52 of the mouthpiece 26. This shank 52 is typically of a diameter just slightly less than the corresponding inner diameter of the cover 24 (between inner surfaces 53 of the cover 24). The shank 52 also includes at least one recess 54, for engaging a correspondingly shaped protrusion(s) 57, typically extending continuously around the inner surface 53 (FIG. 4) of the cover 24. The dimensioning of the shank 52 and cover 24, coupled with the corresponding recess 54 and protrusion(s) 57, allows the cover 24 to be retained on the mouthpiece 26 in a frictional engagement, whereby removal of the cover 24 on the mouthpiece 26 requires minimal force. The cover 24 may include cylindrical finger grip grooves 58 to assist the user in gripping the cover 24 when use of the inhaler portion 22 is desired.

The cover 24 and mouthpiece 26 are typically designed, where reattachment of the cover 24 to the mouthpiece 26 is not possible, as either the recess 54 or protrusion(s) 57 are damaged during cover 24 separation, whereby they are no longer functional for maintaining a the aforementioned engagement. Alternately, the cover 24 and mouthpiece 26 could include portions of thread like structures, at least one of which is stripped upon separation of the inhaler portion 22 from the cover 24, or either of the cover 24 or the mouthpiece 26 includes one-way ratchet-like structures that damage upon the aforementioned separation. This ensures that the inhaler portion 22 will be a single-use one time device. Testing the apparatus 20 to make sure that it has not been used, accordingly, involves simply, turning the apparatus 20 upside down, with the cover 24 facing the ground. If the cover 24 falls off easily, this is a relatively certain indication that the inhaler portion 22 has been used.

Figure 4:
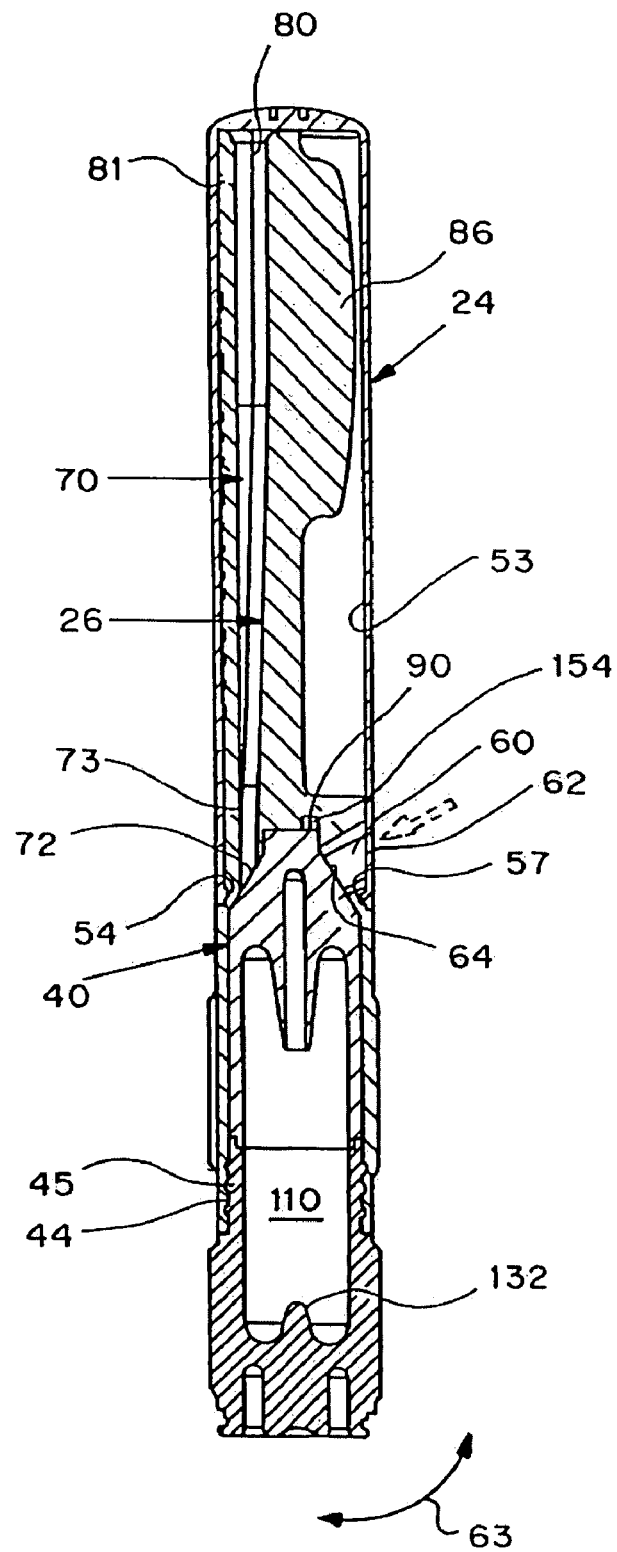
FIG. 4 is a cross sectional view of the apparatus of FIG. 1 showing it in a closed position.

Turning also to FIGS. 3A–3E and 4 (the apparatus 20 is shown in the closed or stowed position in FIG. 4), port 60, extends through the shank 52. The port 60 includes an inlet opening 62 (through which ambient air enters the inhaler portion 22), over which the cover 24 extends. This allows the inhaler portion 22 to be separated from the cover by simply popping/pulling it off, or, alternately by twisting or rotating it off (in the direction of double headed arrow 63), if a mechanical thread system (for example, a high-helix thread engagement) is employed in the inhaler portion 22 and the cover 24.

The cover 24 extends over and the inlet opening 62 and port 60, so as to engage the shank 52 beyond the inlet opening 62, such that the port 60 and inlet opening are under cover and not exposed to the ambient environment until use (i.e., separation of the inhaler portion 22 from the cover 24) is desired. Since under cover, the chance of dust particles or other particulates that could get into the port 60 and clog it is minimized. The port 60 is, for example, rectangular in cross section, with other cross-sectional shapes, such as round, also suitable. The port 60 terminates in an inner opening 64, corresponding in shape and dimensions with the opening 122 (FIG. 6B) in the cartridge 32.

The mouthpiece 26, in its tube section 28 includes the shank 52, with a discharge tube 70 for particles (from the chamber 110, detailed below), that extends therethrough. As shown in FIG. 5A, the tube 70 includes an opening 72, typically a rounded or circular opening at its inner end 73. Moving outward, the tube 70 has a constant diameter portion 74, followed by a tapered portion 76, and a straight portion 78, terminating in an opening 80, at the outer end 81, through which particles leave the inhaler portion 22 and enter into the oral cavity of a user. These three portions 74, 76 and 78, couple to deagglomerate residual particle aggregations within the particle flow and control the velocity at which the particles are discharged into the oral cavity. Additionally, the lengths of each portion 74, 76 and 78 are optimized so as not to give rise to flow separation (backwards flow that creates vortices or eddies).

The constant diameter portion 74 is of a constant diameter and of a length sufficient for providing the particles with a straight conduit entrance for particle/gas acceleration and the development of a high-shear flow field. This portion is typically oval or rounded in cross section, as shown in FIG. 5B. This geometry allows for the obliteration of most of the residual agglomerated particles.

The tapered portion 76 is tapered outward (toward outer opening 80), typically at included angles of approximately 3 to 7 degrees, and for example approximately 4 degrees to achieve, for example, a 2:1 aspect ratio. At this aspect ratio, there can be transitioning of the velocity of the particle stream traveling in this tube 70. This tapered portion 76, for example, originates with an oval cross-section (FIG. 5B) and tapers outward to a bean or kidney shaped cross section, as shown in FIG. 5C.

The straight portion 78 is of constant dimensions. This allows for the collimation and velocity control of the particle stream leaving the tube 70. This portion 78 is typically in a bean or kidney shape in cross section, as shown in FIG. 5D, similar to that of the opening 80. However, other shapes are also sufficient, provided they allow for control of the velocity of the particle stream.

A bulb 86 on the outside of the tube section 28, typically a raised oval or other rounded shape, functions as a tongue depressor, as well as the mouthpiece discharge tube locator. Specifically, as shown in detail in FIGS. 3C–3E, 4 and 7B, this shape and dimensioning for the bulb 86 keeps the tongue down, so as not to block particulate flow in the mouth (oral cavity). The shank 52, in particular where it is of greater diameter than the tube 70, serves as a stop surface for abutment of the lips of a user, allowing the lips to form a seal around the tube section 28 at this point for suction, to enhance inhalation. Alternately, there can be a protrusion on the tube section 28, on the side opposite the bulb 86 (i.e., tongue depressor), that serves as a stop surface for the lips, allowing the lips to form a seal around the tube section 28 at this point for suction, to enhance inhalation.

The interior bore 40 of the mouthpiece 26 is correspondingly shaped with respect to the shape of the head portion 102 (FIGS. 6A–6C) of the cartridge 32. This bore 40 includes an indented slot 90 (FIGS. 4 and 7B) that allows a correspondingly dimensioned key 154 from the cartridge 32 to be detained therein, while typically allowing for rotations of the cartridge 32 in the mouthpiece 26 up to 90 degrees, in order that the inhaler portion 22 be moved from a closed or stowed position (shown in FIG. 4), to an open or inhale position (shown in FIGS. 7A and 7B), for inhalation and transport of particles to the lungs. Detents (not shown), typically positioned 90 degrees from each other, extend into the surface 94 of the inner bore 40. These detents are cooperatingly configured to engage berms 150 on the cartridge 32, upon the cartridge 32 being rotated into the open position (detailed below). These detents typically include radial or rounded edges, allowing for movement of the cartridge 32 with respect to the mouthpiece 26 (and vice versa), between the open and closed positions. Alternately, these detents, if provided with square or sharp edges, will be one way, and thus, not allowing for movement back to the closed position (FIG. 4) from the open position (FIG. 7B), whereby the apparatus 20 is a single or one-time use apparatus.

FIGS. 6A–6C show the cartridge 32 in detail. The cartridge 32 is typically formed from a head portion 102 and a tail portion 104, that can be in a snap-together frictional assembly, welded together or joined together by other conventional fastening techniques and/or mechanisms. The head 102 and tail 104 portions when joined together house a chamber 110 in their combined interior.

An inlet conduit 112, for intake air extends into the chamber 110, in the head portion 102. This inlet conduit 112 is formed of a feed channel 114, correspondingly shaped with respect to the port 60, for alignment when the inhaler portion 22 is in the open position, and a collimation tube 116, that extends from the feed channel 114 (through opening 117*a*) into the chamber 110 (through opening 117*b*).

An exit tube 118 for particles extends from the chamber 110 (via opening 119) to the outer surface 120 of the cartridge 32. This exit tube 118 terminates in an opening 122 dimensioned to correspond with the opening 72 in the mouthpiece 26 for particle flow therethrough, when the cartridge 32 and mouthpiece 26 are aligned when the inhaler portion 22 is in the open position (FIG. 7B).

Within the chamber 110, are ridges 130*a*, 130*b*, typically rounded in shape. In the tail portion 104, the ridges 130*b* extend to form a central protrusion 132. This protrusion 132 is typically cone shaped, and coupled with the ridges 130*a*, 130*b*, creates vortices for the particles (represented by arrows 134) from the airflow through the collimation tube 116 (represented by arrows 136). By creating vortices, the particles deagglomerate and are suspended in a concentration of the uniform dry powder aerosol. This effectively maximizes emptying of the chamber 110 and allows particles to be entrained in the breadth stream.

Within this chamber 110, inhalant, typically in a dry powder form, is held. This inhalant can be, for example, Technosphere™ encapsulated bioactive molecule(s) (Pharmaceutical Discovery Corporation, Elmsford, N.Y. 10523), as described in commonly owned U.S. Provisional Patent Application No. 60/349,628, entitled: COMPOSITIONS FOR TREATMENT OR PREVENTION OF BIOTERRORISM, the disclosure of which is incorporated by reference herein, or Atropine, antibiotics, such as penicillin, doxycycline, Ciprofloxacin and fluoroquinolones, encapsulated in Technospheres™, these Technospheres™ and methods for their manufacture disclosed in U.S. Pat. Nos. 5,352,461, 5,503,852 and 6,071,497, all three of these U.S. Patents incorporated by reference herein.

The head portion 102 is typically formed of a cylindrical portion 140, a conical portion 142 (for example, at approximately a 60–70 degree included angle), and a disc portion 144, over the conical portion 142. Riblets 45 typically extend around the cylindrical portion 140 so as to engage corresponding riblets 44 of the mouthpiece 26, and maintain the frictional and rotating engagement of the cartridge 32 and mouthpiece 26 as detailed above. The conical portion 142 includes an opening 146 for the feed channel 114, that is typically rectangular to attain optimal flow control, as well as the opening 122 for the exit tube 118.

Berms 150, protrude a slight distance from the surface 151 of the conical portion 142. By extending this slight distance, coupled with the material of the cartridge, and thus the berm 150, the berms 150 behave in a spring like manner. The berms 150 are typically of square or sharp edges 152, but could also be radial or rounded at their edges. The berms 150 are correspondingly dimensioned for the openings 64, 72 of the mouthpiece 26, in which they seat when the apparatus 20 is in the closed position. (The openings 64, 72 typically include radial or rounded edges to allow rotation of the cartridge 32 in the mouthpiece 26 from the closed to the open position). The berms 150 ultimately rest in the detents (as detailed above),with the spring like behavior of the berms 150 providing tactile sensitivity that the cartridge 32 and mouthpiece 26 are no longer engaged in the closed initial position and the open position has been reached. These berms 150 are typically positioned 180 degrees from each other (although other positionings are also possible), this 180 degrees corresponding to the positions of the openings 64, 72 of the mouthpiece and the respective detents on the mouthpiece 26.

A key 154 extends from the disc portion 144. The key 154 is typically in a crescent shape, and fits within the slot 90 (FIGS. 4 and 7B) in the mouthpiece 28, the slot 90 serving as a boundary for the key 154, and accordingly, having sufficient space to limit rotation of the cartridge 32 with respect to the mouthpiece 26 (and vice versa) to for example 90 degrees (in order that the rotation be between open and closed positions).

The tail portion 104 includes the ridged collar section 49, as detailed above. Additionally, there are threads 158 or ring detents at the end of the tail portion 104, that can engage corresponding threads 159 or berms on the cover 24, to keep the cover on the inhaler portion 22. Alternately, this section of the tail potion 104 and corresponding portion of the cover 24 can be made to permanently lock up once joined together, thus promoting one-time use for the apparatus 20, as shown in FIGS. 7A and 7B. However, this attachment of the cover 24 to the tail portion 104 is optional, as normal operation of the inhaler portion 22 does not require the cover 24 to be attached to the tail portion 104.

All of the aforementioned components, the cover. 24 mouthpiece 26 and cartridge 28, and all structures thereon and/or therein are typically made of plastics, polymers or the like, with one such plastic being acetal plastic, for example DELRIN® 500 and "Antistatic" CELCON® plastics. While these plastics are listed, multiple other plastics, polymers and other materials are also suitable for the components mentioned herein. These plastics, polymers and other materials can be selected for example, based on the composition that will be in the chamber 110, environmental and storage factors, and the like. These components are typically formed by techniques such as molding and for example, injection molding.

Turning specifically to FIGS. 7A and 7B, there is detailed the inhaler portion 22 in an open position, ready for use (inhalation of the contents of the chamber 110). As shown here, the feed channel 114 and exit tube 118 are positioned in the cartridge 32, that having been rotated, are respectively aligned with the inlet port 60 and the discharge tube 70. This alignment in the open position, creates a flow pathway for inhalation, from inlet opening 62 (for intake of ambient air), through to the chamber 110, where a particle stream is created, and through the discharge tube 70 of the mouthpiece 26, where the particle stream in inhaled for ultimate delivery to the lungs, including the deep lungs. The inlet port 60, coupled with the feed channel 114, and the exit tube 118, are typically angled at an angle Θ with respect to the each other of approximately 0 to 180 degrees, and for example, approximately 45 degrees, to avoid large backpressures, that inhibit airflow along the flow pathway.

Figure 8:
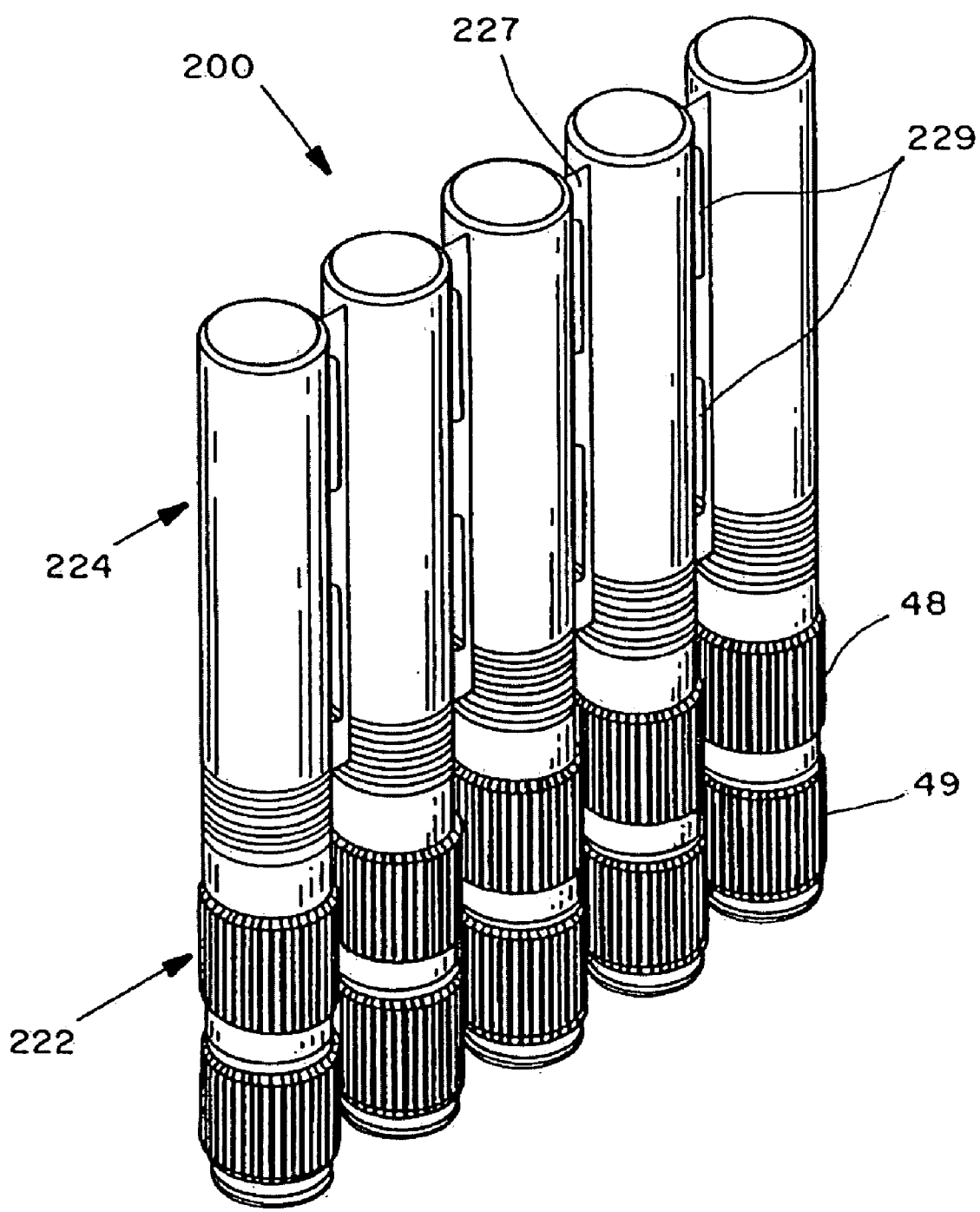
FIG. 8 is an isometric view second embodiment of an apparatus disclosed herein.
Figure 9:
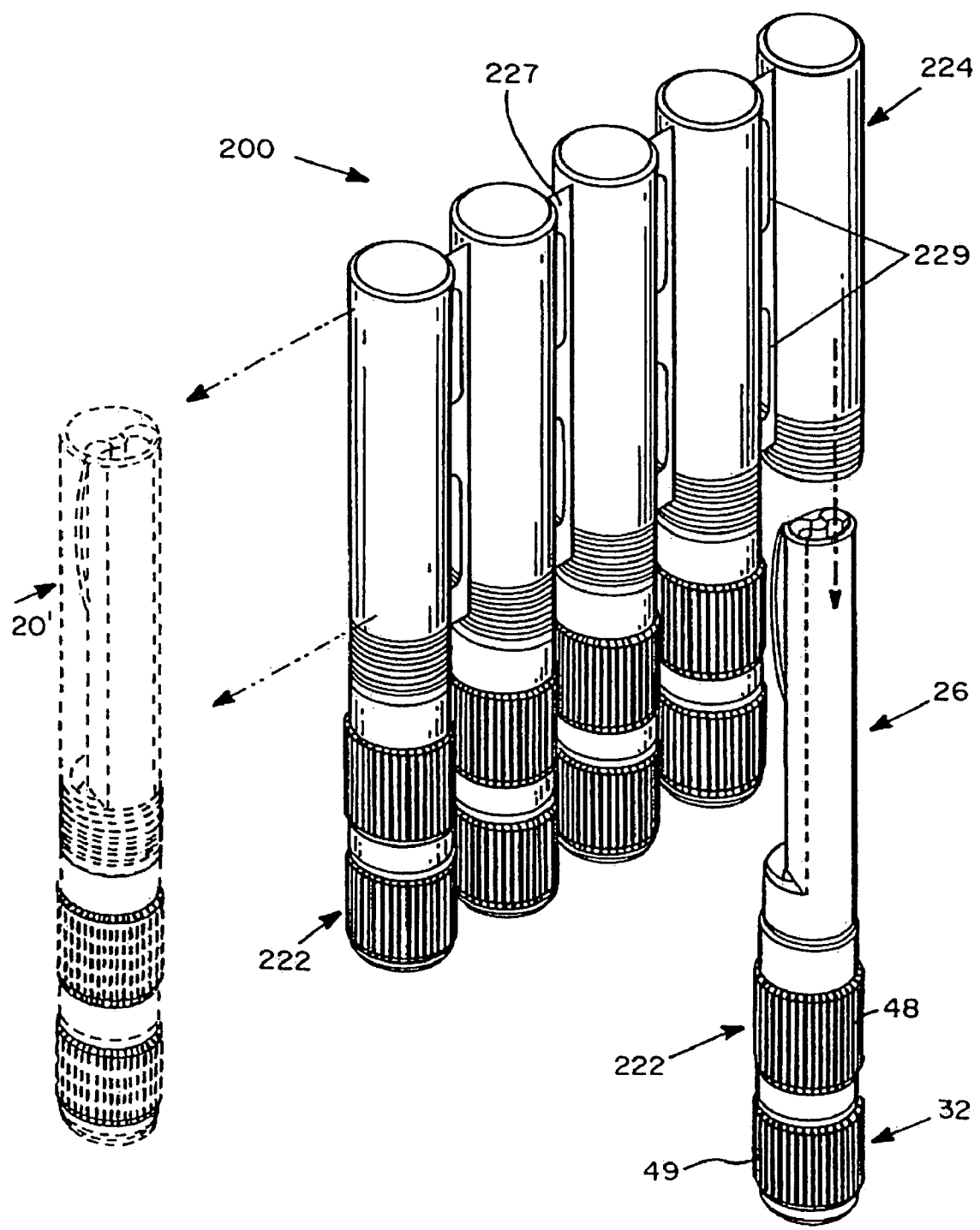
FIG. 9 is an isometric view of the embodiment of FIG. 8, showing removal of an inhaler portion.

FIGS. 8 and 9 show a multiple unit system 200. Here, single inhaler portions 222, similar in all aspects to inhaler portions 22 (detailed above), are in covers 224, similar to covers 24 (detailed above), that are joined as a single unit. The covers 224 include weakened portions 227 and openings 229 between them, allowing for easy separation into individual units 20′.

While preferred embodiments of an apparatus, components and methods, have been described above, the description of the apparatus, components and methods above is exemplary only. Those skilled in the art will recognize, or be able to ascertain using no more than routine experimentation, many equivalents to the specific embodiments of the invention described herein. Such equivalents are intended to be encompassed by the following claims.

We claim:

1. A cartridge for use in an inhalation apparatus comprising a mouthpiece, the mouthpiece including a central bore having at least one open end and a tube for carrying particles to the oral cavity of a user;

the cartridge including at least one portion for receipt in the bore of the inhalable device in a rotatable engagement, and a chamber for storing an inhalable substance;

wherein the mouthpiece and the cartridge are rotatable with respect to each other, from a first position, where the chamber is closed to an ambient environment and the mouthpiece tube, to a second position, where a flow pathway from the ambient environment to the tube of the mouthpiece through the chamber, has been opened;

the mouthpiece and the cartridge including cooperatingly configured structures to retain the second position once the second position has been reached.

2. The cartridge of claim 1, additionally comprising a cover, the cover adapted for covering the mouthpiece wherein the cover and the cartridge include cooperatingly configured structures for retaining the cover in an engagement with the cartridge, once the cover has been placed on the cartridge.

* * * * *